(12) United States Patent
Schaeffer et al.

(10) Patent No.: US 9,259,336 B2
(45) Date of Patent: Feb. 16, 2016

(54) STENT WITH A CRUSH-RESISTANT ZONE

(75) Inventors: Darin G. Schaeffer, Bloomington, IN (US); Scott E. Boatman, Bloomington, IN (US); Jay A. Dittman, Indianapolis, IN (US); David Earnest Hartley, Subiaco (AU)

(73) Assignee: Cook Medical Technologies LLC, Bloomington, IN (US)

( * ) Notice: Subject to any disclaimer, the term of this patent is extended or adjusted under 35 U.S.C. 154(b) by 2186 days.

(21) Appl. No.: 11/810,533

(22) Filed: Jun. 6, 2007

(65) Prior Publication Data
US 2007/0293940 A1    Dec. 20, 2007

Related U.S. Application Data

(60) Provisional application No. 60/811,159, filed on Jun. 6, 2006.

(51) Int. Cl.
*A61F 2/06* (2013.01)
*A61F 2/856* (2013.01)
(Continued)

(52) U.S. Cl.
CPC . *A61F 2/856* (2013.01); *A61F 2/07* (2013.01); *A61F 2/91* (2013.01); *A61F 2/915* (2013.01); *A61F 2/954* (2013.01); *A61F 2/958* (2013.01); *A61F 2002/072* (2013.01); *A61F 2002/075* (2013.01); *A61F 2002/821* (2013.01); *A61F 2002/91525* (2013.01); *A61F 2002/91558* (2013.01); *A61F 2002/91566* (2013.01); *A61F 2220/0016* (2013.01); *A61F 2220/0075* (2013.01); *A61F 2250/0018* (2013.01); *A61F 2250/0029* (2013.01); *A61F 2250/0039* (2013.01)

(58) Field of Classification Search
CPC .......................... A61F 2/954; A61F 2002/065
USPC ......... 623/1.11, 1.13, 1.15, 1.31, 1.35, 23.64, 623/23.65
See application file for complete search history.

(56) References Cited

U.S. PATENT DOCUMENTS

| 5,064,435 A | 11/1991 | Porter |
| 5,282,824 A | 2/1994 | Gianturco |

(Continued)

FOREIGN PATENT DOCUMENTS

| CA | 2619429 | 3/2007 |
| EP | 0 712 614 B1 | 5/1996 |

(Continued)

OTHER PUBLICATIONS

International Search Report and Written Opinion of the International Searching Authority for International Application PCT/US2007/013361.

(Continued)

*Primary Examiner* — Thomas J Sweet
*Assistant Examiner* — Seema Mathew
(74) *Attorney, Agent, or Firm* — Brinks Gilson & Lione

(57) ABSTRACT

An endoluminal prosthesis system for a branched body lumen comprises a branch vessel prosthesis. The branch vessel prosthesis is deployable within a branch vessel body lumen and comprises a stent having a generally tubular body portion, a flareable proximal end portion, and a coupling portion disposed intermediate the body portion and the flareable portion. The coupling portion is preferably more crush-resistant than the body portion.

20 Claims, 11 Drawing Sheets

(51) Int. Cl.

| | | |
|---|---|---|
| *A61F 2/07* | (2013.01) | |
| *A61F 2/91* | (2013.01) | |
| *A61F 2/915* | (2013.01) | |
| *A61F 2/954* | (2013.01) | |
| *A61F 2/958* | (2013.01) | |
| *A61F 2/82* | (2013.01) | |

(56) References Cited

U.S. PATENT DOCUMENTS

| | | | |
|---|---|---|---|
| 5,334,217 A | | 8/1994 | Das |
| 5,609,627 A | | 3/1997 | Goicoechea et al. |
| 5,617,878 A | | 4/1997 | Taheri |
| 5,676,670 A | * | 10/1997 | Kim ............... A61B 17/320016 606/108 |
| 5,683,451 A | | 11/1997 | Lenker |
| 5,718,713 A | | 2/1998 | Frantzen |
| 5,741,327 A | | 4/1998 | Frantzen |
| 5,755,778 A | | 5/1998 | Kleshinski |
| 5,797,920 A | * | 8/1998 | Kim ............... A61B 17/320016 606/108 |
| 5,824,040 A | | 10/1998 | Cox et al. |
| 5,843,164 A | | 12/1998 | Frantzen et al. |
| 5,843,175 A | | 12/1998 | Frantzen |
| 5,868,777 A | | 2/1999 | Lam |
| 5,868,780 A | | 2/1999 | Lashinski et al. |
| 5,984,955 A | | 11/1999 | Wisselink |
| 6,027,526 A | * | 2/2000 | Limon et al. ................. 623/1.15 |
| 6,036,702 A | * | 3/2000 | Bachinski ........ A61B 17/00234 606/153 |
| 6,042,606 A | | 3/2000 | Frantzen |
| 6,110,198 A | | 8/2000 | Fogarty et al. |
| 6,113,612 A | | 9/2000 | Swanson et al. |
| 6,168,619 B1 | | 1/2001 | Dinh et al. |
| 6,210,429 B1 | | 4/2001 | Vardi et al. |
| 6,221,090 B1 | | 4/2001 | Wilson |
| 6,231,598 B1 | | 5/2001 | Berry et al. |
| 6,241,757 B1 | * | 6/2001 | An ............................ A61F 2/90 623/1.1 |
| 6,245,100 B1 | | 6/2001 | Davila et al. |
| 6,264,682 B1 | | 7/2001 | Wilson et al. |
| 6,273,910 B1 | * | 8/2001 | Limon ..................... A61F 2/91 623/1.15 |
| 6,296,661 B1 | | 10/2001 | Davila et al. |
| 6,315,708 B1 | | 11/2001 | Salmon et al. |
| 6,325,826 B1 | | 12/2001 | Vardi et al. |
| 6,428,569 B1 | | 8/2002 | Brown |
| 6,464,720 B2 | | 10/2002 | Boatman et al. |
| 6,482,227 B1 | | 11/2002 | Solovay |
| 6,485,513 B1 | | 11/2002 | Fan |
| 6,524,335 B1 | | 2/2003 | Hartley et al. |
| 6,579,309 B1 | | 6/2003 | Loos et al. |
| 6,582,458 B1 | | 6/2003 | White et al. |
| 6,585,758 B1 | | 7/2003 | Chouinard et al. |
| 6,602,284 B2 | | 8/2003 | Cox et al. |
| 6,613,079 B1 | | 9/2003 | Wolinsky et al. |
| 6,638,300 B1 | | 10/2003 | Frantzen |
| 6,676,697 B1 | | 1/2004 | Richter |
| 6,706,062 B2 | | 3/2004 | Vardi et al. |
| 6,740,113 B2 | | 5/2004 | Vrba |
| 6,743,252 B1 | | 6/2004 | Bates et al. |
| 6,764,506 B2 | | 7/2004 | Roubin et al. |
| 6,786,922 B2 | | 9/2004 | Schaeffer |
| 6,890,349 B2 | | 5/2005 | McGuckin, Jr. et al. |
| 6,945,994 B2 | | 9/2005 | Austin et al. |
| 6,964,681 B2 | | 11/2005 | Murray, III |
| 7,160,319 B2 | | 1/2007 | Chouinard et al. |
| 7,220,275 B2 | | 5/2007 | Davidson et al. |
| 7,582,111 B2 | | 9/2009 | Krolik et al. |
| 2001/0007954 A1 | | 7/2001 | Shaolian et al. |
| 2001/0047201 A1 | * | 11/2001 | Cox et al. ..................... 623/1.16 |
| 2002/0007102 A1 | | 1/2002 | Salmon et al. |
| 2002/0058986 A1 | | 5/2002 | Landau et al. |
| 2002/0058988 A1 | * | 5/2002 | Fischell et al. ............... 623/1.15 |
| 2003/0083734 A1 | | 5/2003 | Friedrich et al. |
| 2003/0088310 A1 | | 5/2003 | Hansen et al. |
| 2003/0125799 A1 | * | 7/2003 | Limon ......................... 623/1.15 |
| 2003/0130724 A1 | | 7/2003 | De Palma et al. |
| 2003/0163188 A1 | * | 8/2003 | Haverkost ................. A61F 2/90 623/1.11 |
| 2003/0199967 A1 | | 10/2003 | Hartley et al. |
| 2003/0236563 A1 | | 12/2003 | Fifer |
| 2004/0034406 A1 | | 2/2004 | Thramann |
| 2004/0059406 A1 | | 3/2004 | Cully et al. |
| 2004/0093058 A1 | * | 5/2004 | Cottone .................... A61F 2/07 623/1.11 |
| 2004/0176833 A1 | | 9/2004 | Pavcnik |
| 2004/0176837 A1 | * | 9/2004 | Atladottir ............... A61F 2/856 623/1.35 |
| 2004/0230287 A1 | | 11/2004 | Hartley et al. |
| 2004/0243218 A1 | | 12/2004 | Schaeffer |
| 2004/0254627 A1 | | 12/2004 | Thompson et al. |
| 2005/0004647 A1 | | 1/2005 | Bassoe |
| 2005/0131517 A1 | | 6/2005 | Hartley et al. |
| 2005/0131518 A1 | | 6/2005 | Hartley et al. |
| 2005/0131519 A1 | | 6/2005 | Hartley |
| 2005/0149166 A1 | | 7/2005 | Schaeffer et al. |
| 2005/0154447 A1 | | 7/2005 | Goshgarian |
| 2005/0171598 A1 | | 8/2005 | Schaeffer |
| 2005/0209679 A1 | | 9/2005 | Melsheimer |
| 2005/0222668 A1 | | 10/2005 | Schaeffer et al. |
| 2005/0222669 A1 | * | 10/2005 | Purdy ....................... A61F 2/07 623/1.13 |
| 2005/0222670 A1 | | 10/2005 | Schaeffer |
| 2005/0222671 A1 | | 10/2005 | Schaeffer et al. |
| 2006/0058864 A1 | | 3/2006 | Schaeffer et al. |
| 2007/0055358 A1 | | 3/2007 | Krolik et al. |
| 2007/0073376 A1 | * | 3/2007 | Krolik et al. ................ 623/1.11 |
| 2007/0073388 A1 | | 3/2007 | Krolik et al. |
| 2007/0088425 A1 | * | 4/2007 | Schaeffer ................. A61F 2/07 623/1.13 |
| 2007/0179590 A1 | * | 8/2007 | Lu ............................ A61F 2/07 623/1.16 |
| 2009/0234430 A1 | * | 9/2009 | Fleming .................. A61F 2/07 623/1.13 |
| 2009/0306763 A1 | * | 12/2009 | Roeder ..................... A61F 2/07 623/1.13 |
| 2010/0274345 A1 | * | 10/2010 | Rust ......................... A61F 2/07 623/1.13 |
| 2010/0331809 A1 | * | 12/2010 | Sandhu ................... A61F 2/945 604/500 |
| 2012/0116500 A1 | * | 5/2012 | Jang ...................... A61F 2/856 623/1.35 |
| 2012/0239132 A1 | * | 9/2012 | Naor ........................ A61F 2/07 623/1.14 |
| 2013/0338761 A1 | * | 12/2013 | Plowiecki ............... A61F 2/856 623/1.35 |
| 2015/0005870 A1 | * | 1/2015 | Kovach ................... A61L 31/10 623/1.13 |

FOREIGN PATENT DOCUMENTS

| | | |
|---|---|---|
| JP | 3112157 | 9/2000 |
| JP | 2002-537944 | 11/2002 |
| JP | 2005-515834 | 6/2005 |
| WO | WO 98/53761 A1 | 12/1998 |
| WO | WO 99/13808 A1 | 3/1999 |
| WO | WO 2005/034807 A1 | 4/2005 |
| WO | WO 2006/127784 A2 | 11/2006 |

OTHER PUBLICATIONS

Exam Report No. 1 for Australian Patent Application Serial No. 2007258592 dated Feb. 28, 2012, 2 pages.

Exam Report No. 2 for Australian Patent Application Serial No. 2007258592 dated Jul. 10, 2012, 3 pages.

Office Action for Canadian Patent Application Serial No. 2,653,190 dated Nov. 14, 2013, 3 pages.

Office Action for European Patent Application Serial No. 07795816.3 dated Feb. 25, 2011, 3 pages.

Office Action for European Patent Application Serial No. 07795816.3 dated Mar. 25, 2013, 4 pages.

Office Action for European Patent Application Serial No. 07795816.3 dated Jun. 23, 2015, 4 pages.

(56) References Cited

OTHER PUBLICATIONS

Extended Search Report for European Patent Application Serial No. 13154239.1 dated Mar. 21, 2013, 4 pages.

Office Action for European Patent Application Serial No. 13154239.1 dated Aug. 19, 2013, 3 pages.

Office Action with English Translation for Japanese Patent Application Serial No. 2009-514363 dated Jan. 24, 2012, 6 pages.

* cited by examiner

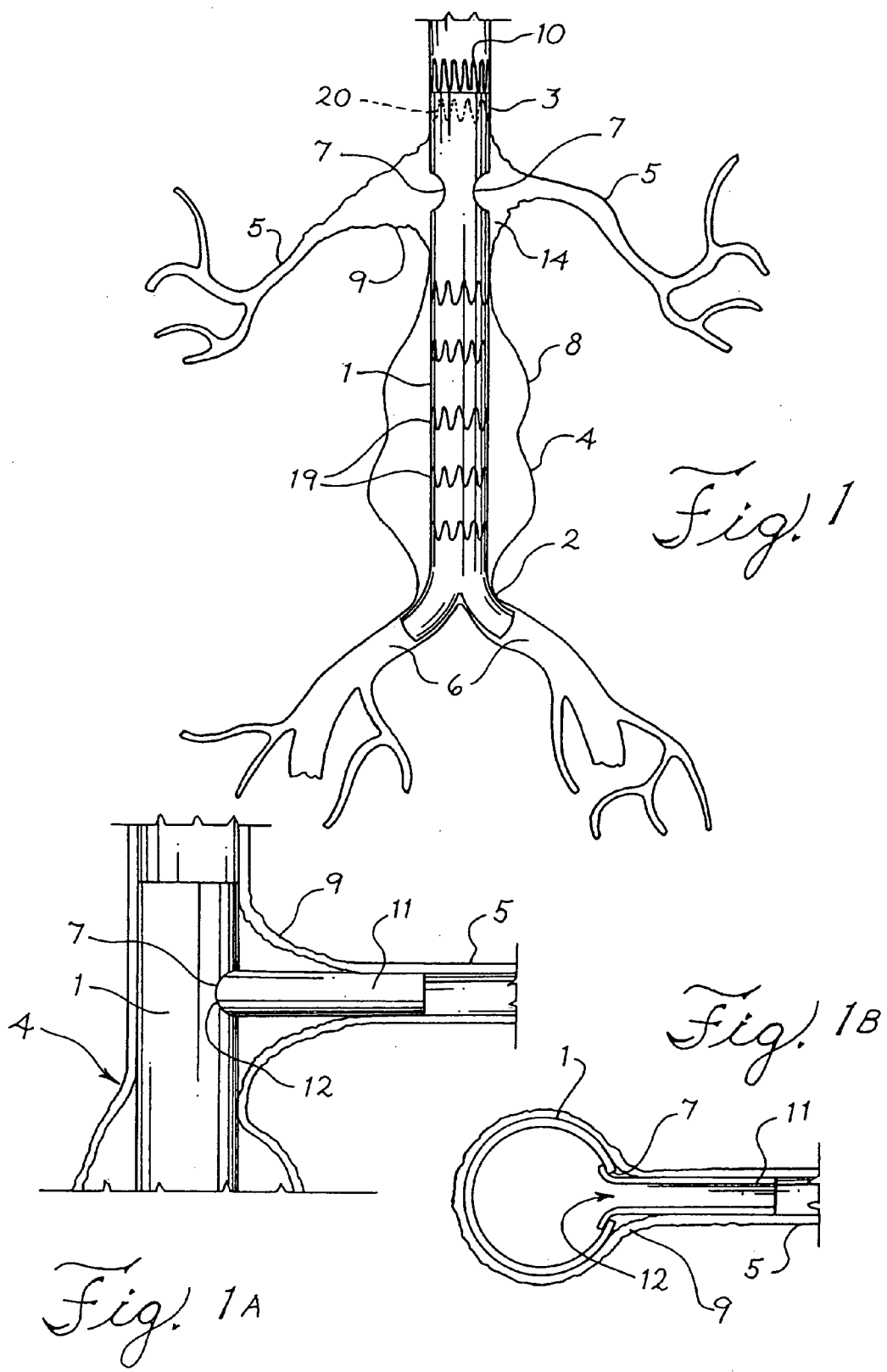

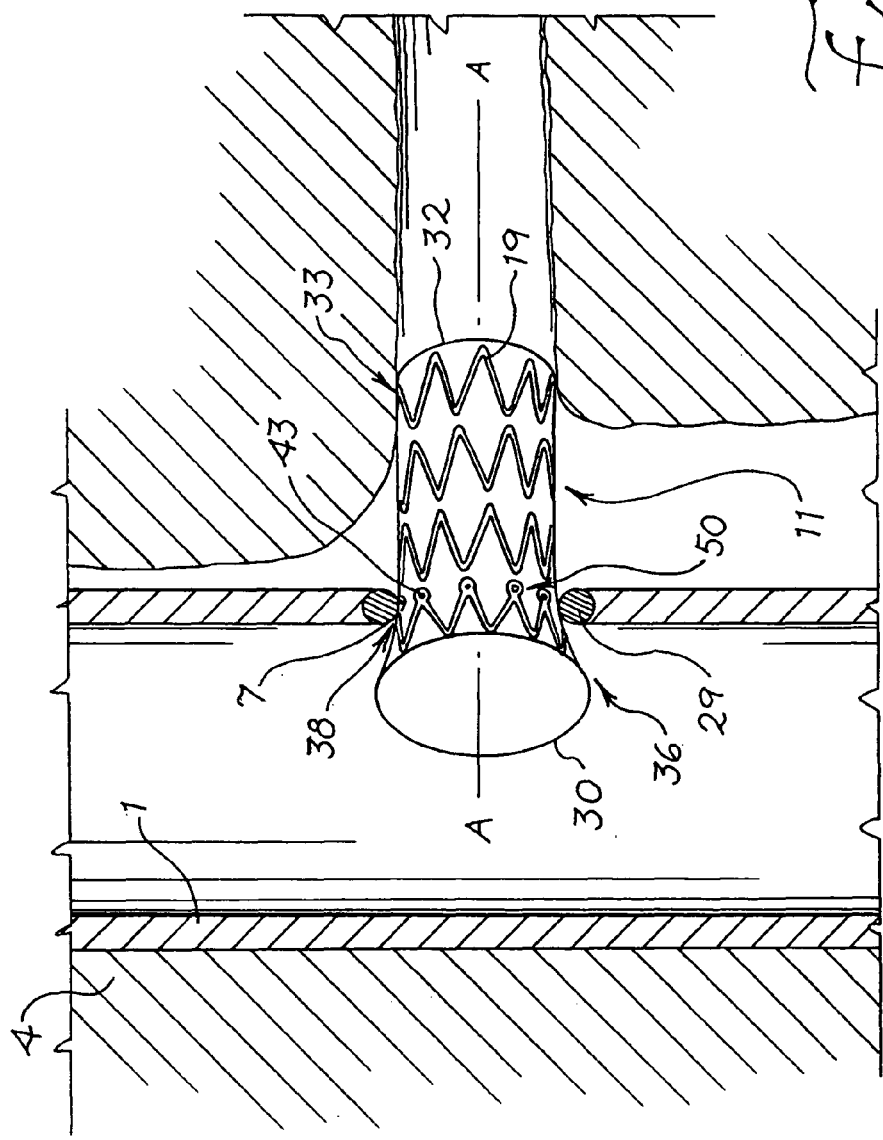

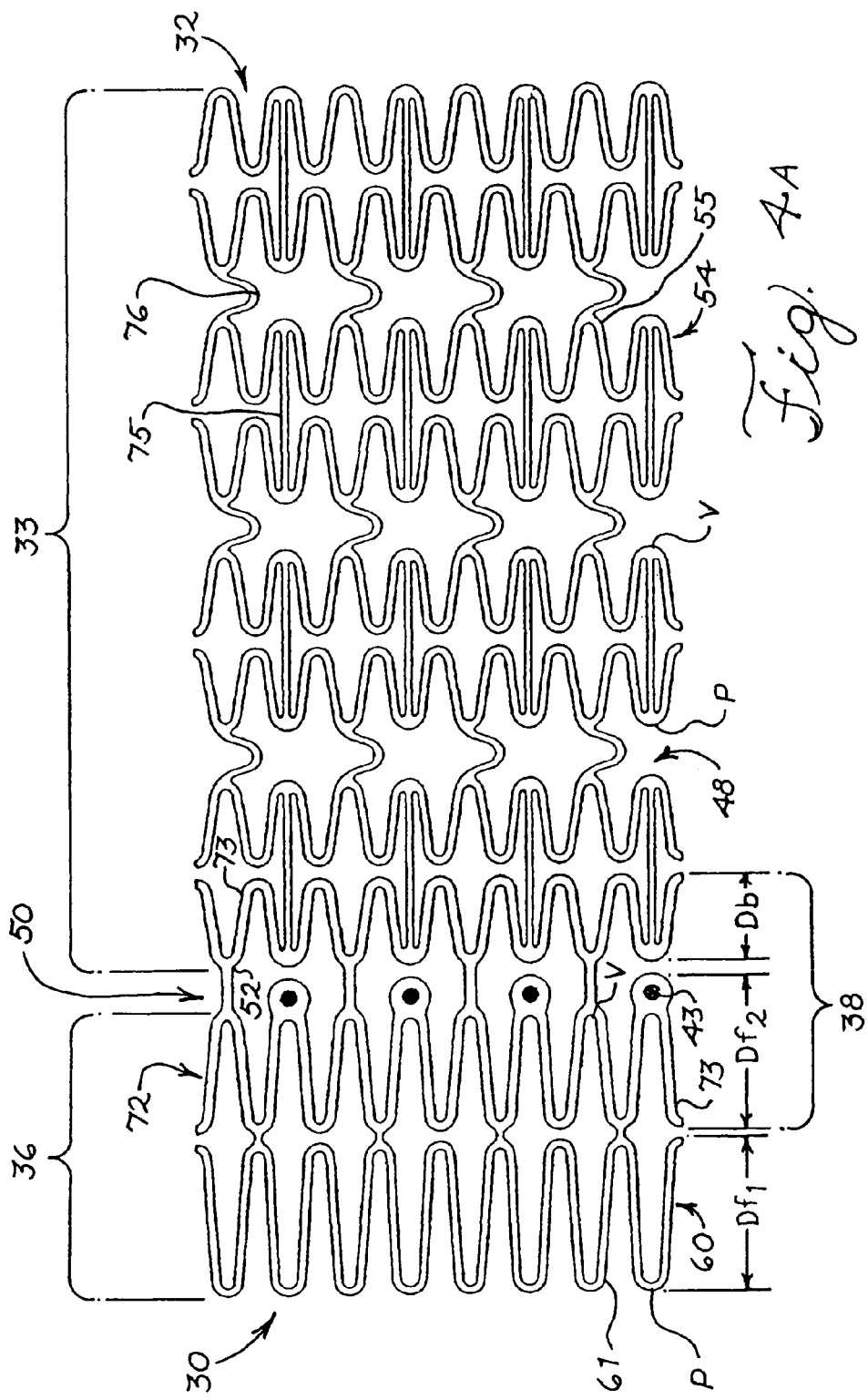

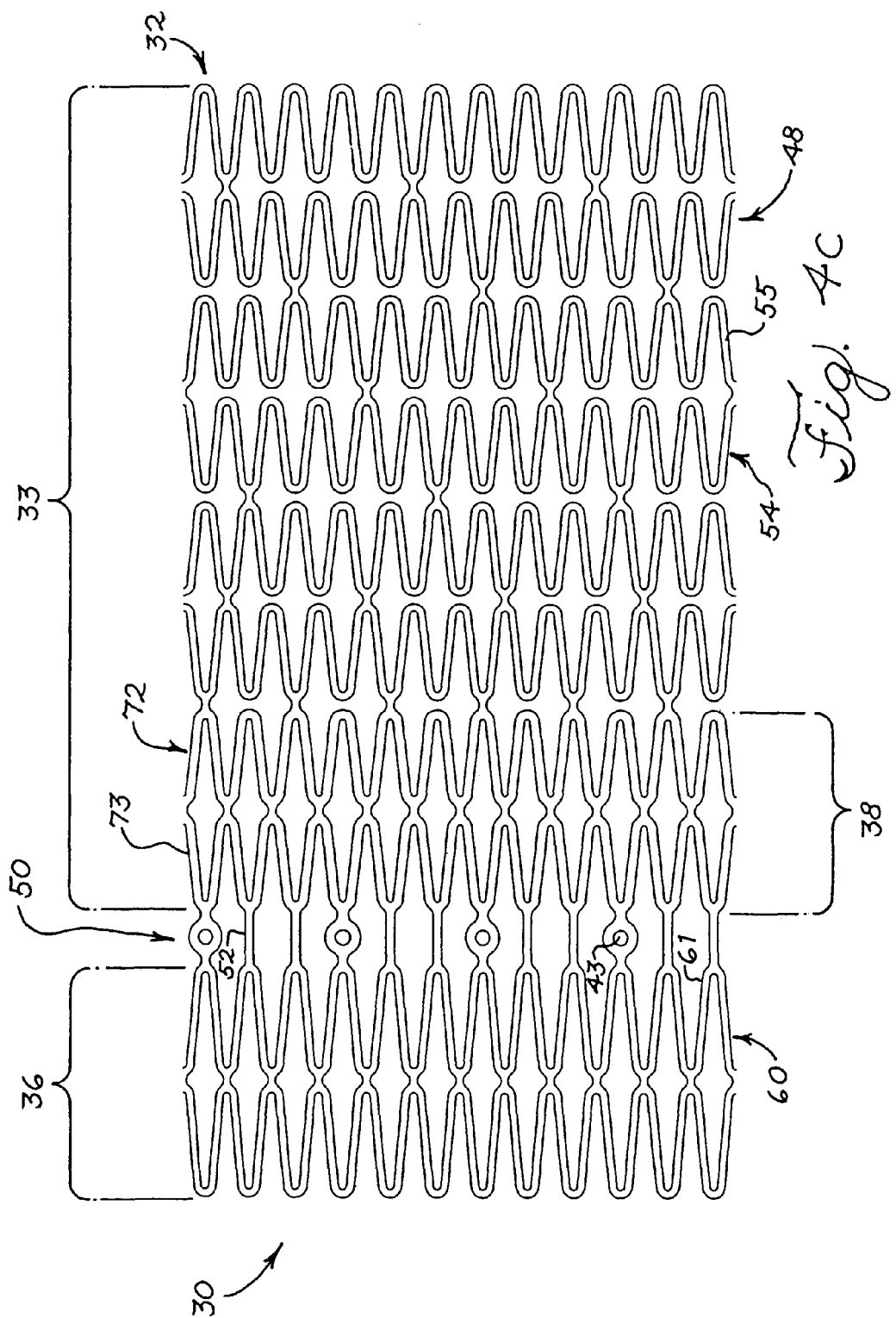

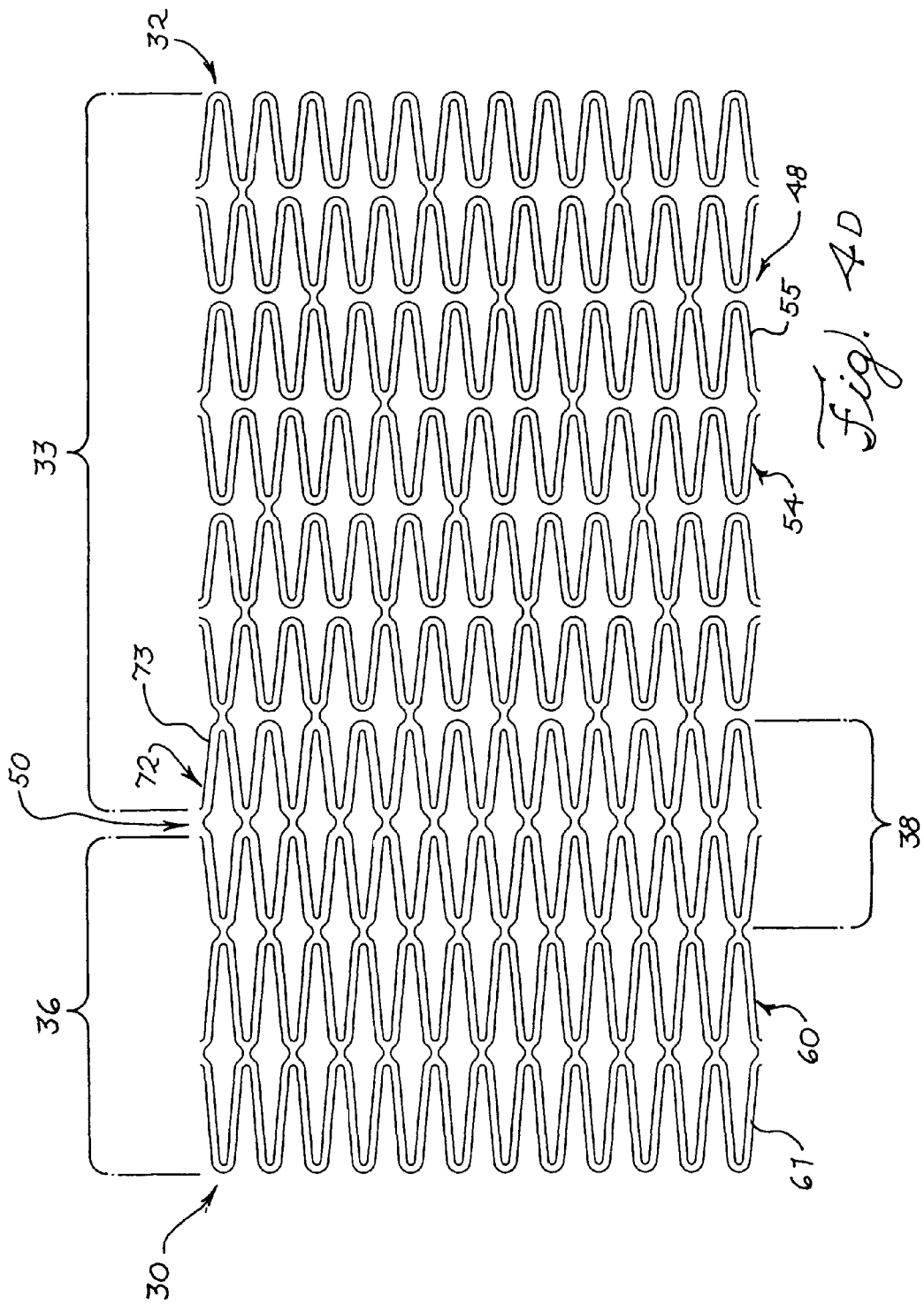

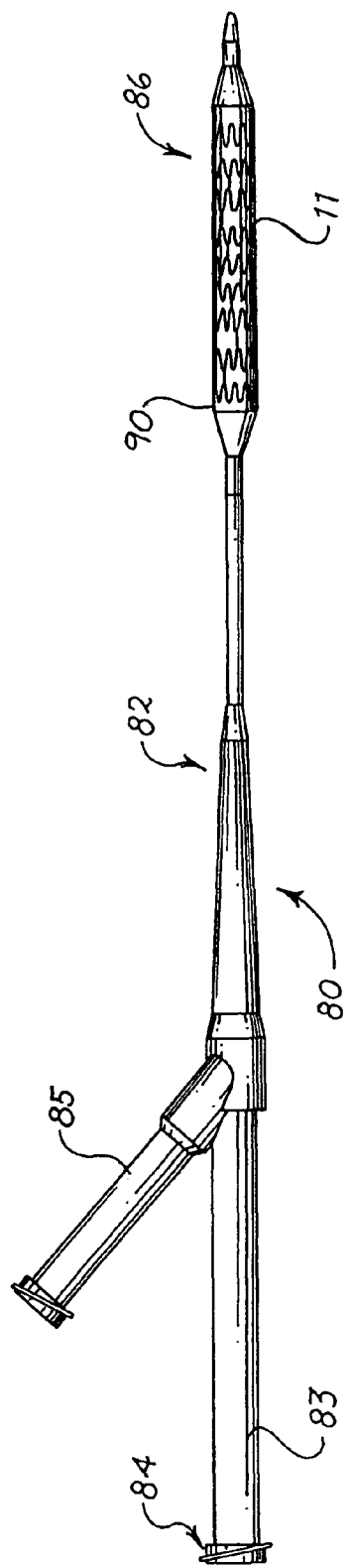
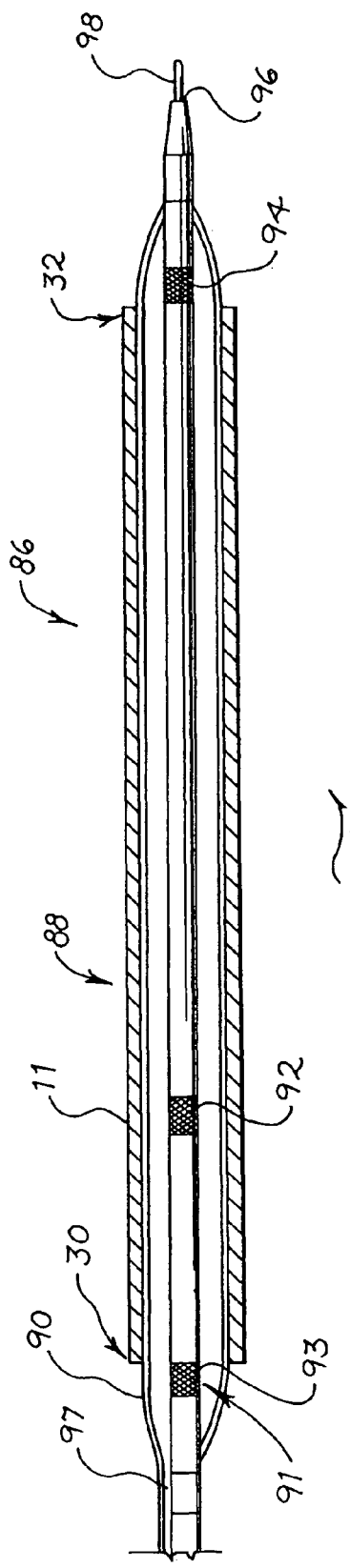
Fig. 6
Fig. 7

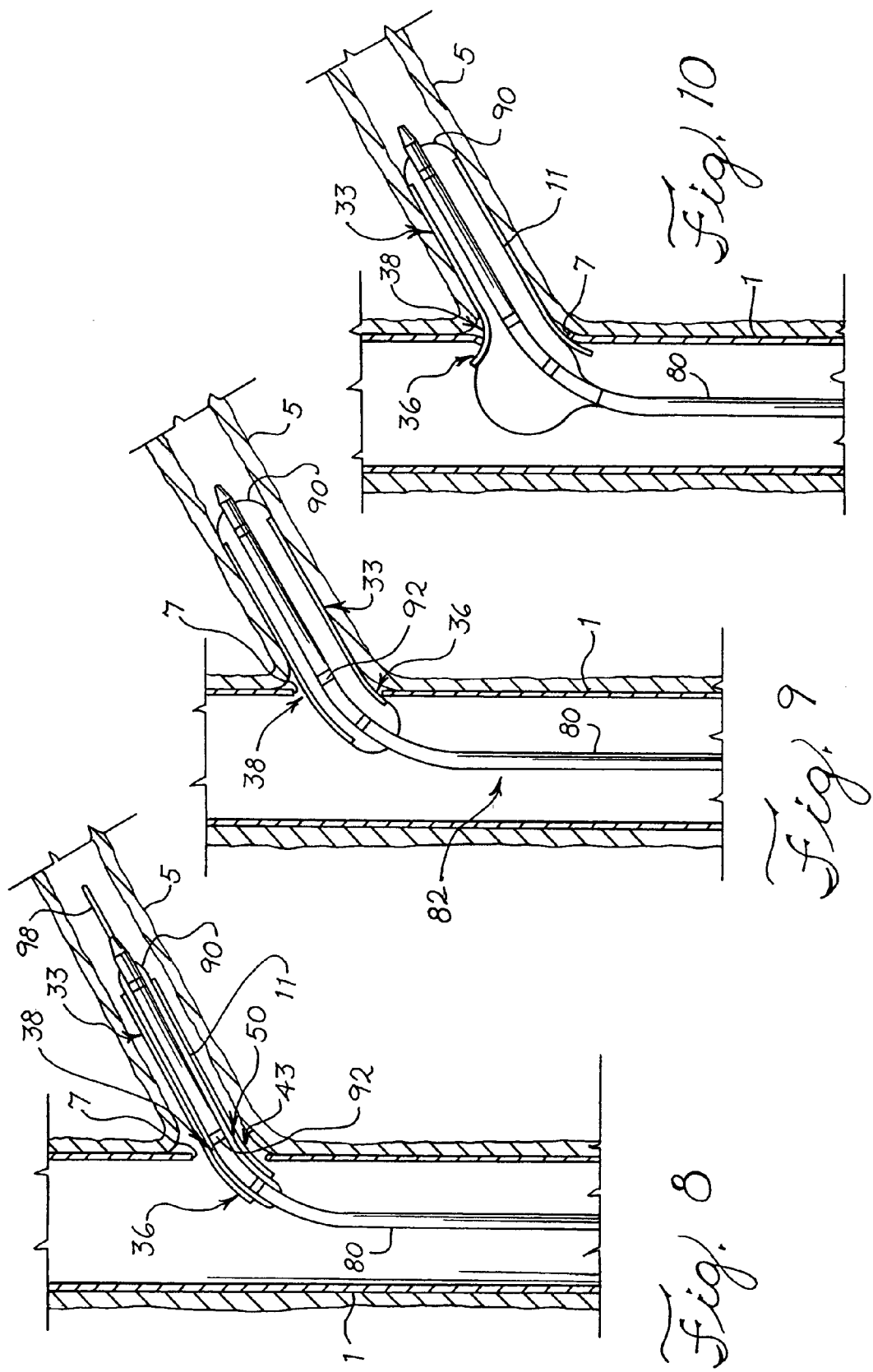

STENT WITH A CRUSH-RESISTANT ZONE

RELATED APPLICATIONS

This application claims the benefit of the filing date under 35 U.S.C. §119(e) of U.S. Provisional Patent Application Ser. No. 60/811,159, filed Jun. 6, 2006, which is incorporated herein by reference.

BACKGROUND OF THE INVENTION

1. Field of the Invention

This invention relates to medical devices, and more particularly, to endoluminal devices and methods for making and using such endoluminal devices.

2. Description of Related Art

The functional vessels of human and animal bodies, such as blood vessels and ducts, occasionally weaken or even rupture. For example, an aortic wall can weaken, resulting in an aneurysm. Upon further exposure to hemodynamic forces, such an aneurysm can rupture, resulting in internal bleeding, and often death.

Various interventions have been provided for weakened, aneurysmal, dissected or ruptured vessels, including surgical interventions and endovascular interventions. Endovascular interventions generally include inserting an endoluminal device or prosthesis such as a stent or stent graft into the damaged or diseased body lumen to provide support for the lumen, and to exclude damaged portions thereof.

The endovascular prosthesis is delivered in a radially compressed configuration using a catheter delivery system. The catheter is introduced into the lumen system remotely of the repair site and the prosthesis is delivered to the repair site intraluminally. The prosthesis is then expanded to engage the luminal wall. The prosthesis may provide some or all of the functionality of the original, healthy vessel and may further preserve any remaining vascular integrity.

An example of a prosthesis that may be used for treating damaged or diseased body lumens is disclosed in PCT Application WO 98/53761, which is herein incorporated by reference. The prosthesis may include a bifurcated stent graft. The stent graft includes a biocompatible graft material and a plurality of longitudinally disposed stents. The stent graft is designed to span and exclude an aortic aneurysm extending between the iliac and renal arteries. Other prostheses that may be used include non-bifurcated stent grafts for spanning and excluding aortic aneurysms within the abdominal aorta or the thoracic aorta.

Often times, a body lumen may be damaged in an area that includes a branch vessel. For example, there are at least three branch vessels extending from the abdominal aorta, each leading to various body organs. These branch vessels include the celiac, mesenteric, and renal arteries. When an aneurysm includes or is adjacent to one or more of these branch vessels, the prosthesis system must be able to exclude the aneurysm while maintaining fluid flow through the branch body lumen.

Various stent grafts have been provided for repairing main body lumens and spanning branch vessels without occluding fluid flow thereto. For example, a main body stent graft may be provided that has one or more fenestrations or apertures in the side wall of the stent graft. The stent graft can be deployed so that the fenestration is aligned with a branch vessel.

In many cases, particularly where the damaged portion is positioned at the junction between the main body lumen and the branch body lumen, or where the ostium of the branch vessel is damaged, a main stent graft is insufficient to adequately repair the luminal system. In these situations, it may be preferable to provide a branch lumen prosthesis for positioning within the branch vessel. The branch lumen prosthesis may be used independently, or in conjunction with a main body prosthesis.

U.S. Published Patent Application Nos. 2005/0222668, 2005/0171598, and 2005/0149166 disclose various systems for repairing branched body lumen systems. Various aspects of each of these disclosures may be used in conjunction with the present invention. U.S. Published Patent Application Nos. 2005/0222668, 2005/0171598, and 2005/0149166 are herein incorporated by reference.

A branch vessel prosthesis should be capable of complying with a variety of challenging and often competing demands. For example, the branch vessel prosthesis should preferably be highly flexible and capable of tracking through and conforming with a highly tortuous luminal environment. If the prosthesis includes a balloon-expandable stent, the stent should be sufficiently resilient so as not to hinder balloon expansion and/or molding.

On the other hand, once the prosthesis is implanted in the body lumen, it must be sufficiently strong and robust to survive a highly dynamic and pulsatile luminal environment that can promote prosthesis damage. This is of particular concern where the branch vessel prosthesis is deployed within a fenestration of a main body prosthesis. During the cardiac cycle, the main body prosthesis will pulse and move with the main body vessel, placing stress on the branch vessel prosthesis at the fenestration. When the main body prosthesis moves, it can exert significant concentrated and localized stresses on the branch vessel prosthesis 11 through the fenestration. Over time, this cyclic wear can cause the branch vessel prosthesis to weaken and eventually to crush under the force of the main body prosthesis, requiring further medical intervention.

SUMMARY

According to an aspect of the present invention, an endoluminal prosthesis system for a branched body lumen is provided and comprises a branch vessel prosthesis that is deployable within a branch vessel body lumen. The branch vessel prosthesis comprises a stent having a generally tubular body portion, a flareable proximal end portion, and a coupling portion disposed intermediate the body portion and the flareable portion. The coupling portion is preferably more crush-resistant than the body portion so that the stent can withstand high luminal stresses present in the ostial region of the vessel branch.

The system may further comprise a main vessel prosthesis that is deployable within a main vessel body lumen and having a main prosthesis lumen and a fenestration for providing fluid communication between the main prosthesis lumen and the branch vessel body lumen. When the main and branch vessel prostheses are used in cooperation to repair a branched body lumen, the coupling portion of the branch vessel prosthesis may be sized and configured to engage the fenestration. The main vessel prosthesis may optionally comprise a reinforcing member that at least partially surrounds a perimeter of the fenestration and is configured to engage the coupling portion of the stent. One or both of the main and branch vessel prostheses may comprise a graft.

According to another aspect of the invention, a prosthesis system may be provided that includes a branch vessel prosthesis comprising a body portion, a flareable end portion, and a coupling portion. The body portion may have a stent configuration comprising at least one body stent ring including a plurality of interconnected body struts. Likewise, the flareable end portion may have a stent configuration comprising at least one flare stent ring including a plurality of interconnected flare struts.

Such a prosthesis may include a coupling portion having a stent configuration comprising at least one coupling stent ring disposed between a flare stent ring and a body stent ring. The coupling stent ring may comprise a plurality of interconnected coupling struts. In some embodiments, the coupling portion may comprise a plurality of coupling stent rings.

According to another aspect of the invention, the coupling struts may be thicker than the body struts. For example, the coupling struts may be radially and/or circumferentially thicker than the body struts. The coupling struts may have a thickness that is at least 10%, at least 20%, or at least 25% thicker than the body struts. In some embodiments, the coupling struts may be radially and/or circumferentially thicker than the flare struts.

According to another aspect of the invention, the body portion may comprise a plurality of longitudinally-interconnected body stent rings, and the coupling portion may comprise a plurality of longitudinally-interconnected coupling stent rings. The interconnection frequency between the coupling stent rings may be greater than the interconnection frequency between the body stent rings adjacent the coupling portion.

In some embodiments, the axial dimension of each of the flare stent rings may be greater than the axial dimension of each of at least two body stent rings adjacent the flareable end portion. For example, the axial dimension of the flare stent rings may increase proximally with the flareable configuration. The axial dimension of each of the flare stent rings may be at least 10%, at least 20%, or at least 40% greater than the axial dimension of each of at least two body stent rings adjacent the flareable end portion. The axial dimension of the proximal-most flare stent ring may be at least 10%, at least 20%, or at least 25% greater than the axial dimension of the distal-most flare stent ring.

According to yet another aspect of the invention, the body stent rings may be interconnected by a plurality of body connector struts and the flare stent rings may be interconnected by a plurality of flare connector struts. The flare connector struts may be thicker than the body connector struts. The thickness of the flare connector struts may be at least 10% greater, at least 20% greater, or at least 25% greater than the thickness of the body connector struts. The flare connector struts may be radially and/or circumferentially thicker than the body connector struts.

BRIEF DESCRIPTION OF THE DRAWINGS

FIG. 1 is a partial cross-sectional view of a main prosthesis disposed in the abdominal aorta;

FIG. 1A is a partial side cross-sectional view of a branched vessel system including a branch vessel prosthesis coupled to a main prosthesis;

FIG. 1B is a top cross-sectional view of a branch vessel prosthesis coupled to a main vessel prosthesis;

FIG. 3 is a partial cross-sectional view of a branch vessel prosthesis deployed within a fenestration of a main vessel prosthesis;

FIG. 6 is a side perspective view of a delivery device for a branch vessel prosthesis;

FIG. 7 is a cross-sectional view of a distal portion of the delivery device of FIG. 6;

FIG. 8 shows a branch vessel prosthesis delivery device inserted into a branch vessel;

FIG. 9 shows the delivery device of FIG. 8 in a partially-deployed state; and

FIG. 10 shows the delivery device of FIG. 8 in a partially-deployed state.

DETAILED DESCRIPTION OF THE INVENTION

Figure 2A:
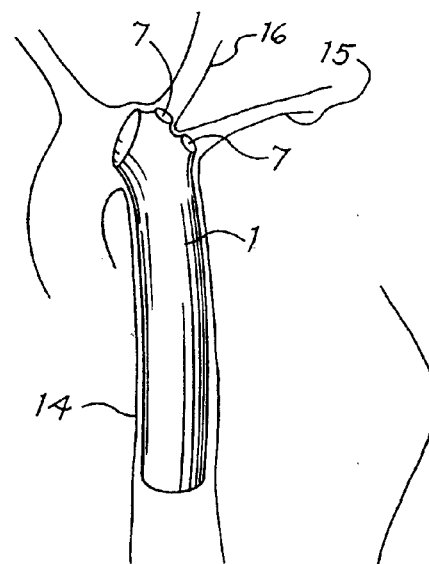
FIG. 2A is a partial cross-sectional view of a main vessel prosthesis in the descending aorta having fenestrations aligned with the left subclavian artery and the left common carotid artery.

Throughout the specification, when referring to a prosthesis, or a structure or component of a prosthesis, the terms "distal" and "distally" shall denote a position, direction, or orientation that is generally downstream in the direction of fluid flow. Accordingly, the terms "proximal" and "proximally" shall denote a position, direction, or orientation that is generally upstream in the direction of fluid flow. Throughout the specification, when referring to a delivery system for a prosthesis, or a structure or component of a delivery system, the terms "distal" and "distally" shall denote a position, direction, or orientation that is generally toward the patient. Accordingly, the terms "proximal" and "proximally" shall denote a position, direction, or orientation that is generally away from the patient.

The terms "crush-resistant" and "crush-resistance" are used throughout the specification and in the appended claims. It is noted that these terms are intended to refer to the measure of the ability of a structure to withstand plastic deformation when the structure is exposed to a concentrated and localized stress. The crush-resistance of a stent may be estimated experimentally by determining the yield strength, or the minimum force required to plastically deform the stent. Crush-resistance may be a function of material selection, as well as stent structure and design.

FIG. 1 illustrates a bifurcated main vessel prosthesis 1 having a distal end 2 and a proximal end 3. The main vessel prosthesis 1 is disposed within the abdominal aorta 4 from a point above the renal arteries 5 to a point where the main prosthesis 1 bifurcates into the iliac arteries 6. The main vessel prosthesis 1 includes two fenestrations 7 or holes that are configured to align with the renal arteries 5. The abdominal aorta 4 and the renal arteries 5 form a branched body lumen system.

The main vessel prosthesis 1 preferably includes a generally fluid-impermeable graft material, for example Dacron. The main vessel prosthesis 1 may further include one or more stents 19, 20. The stents 19, 20 may be positioned internally and/or externally of the graft material. The prosthesis 1 may comprise an internal stent 20 at one or both ends 2, 3. The internal stent 20 provides a smooth external prosthesis surface and helps seal the end of the main vessel prosthesis 1 against an adjoining vascular wall or against an interconnecting module.

Stents 19, 20 may include any suitable stent configuration known in the art. The stents 19, 20 may be balloon-expandable or self-expanding. For example, stents 19, 20 may comprise self-expanding Z stents. The prosthesis may comprise a combination of stents 19, 20 or a single stent having both balloon-expandable and self-expanding properties. The internal stents 20 may comprise barbs (not shown) that extend through the graft material to engage the surrounding vessel wall, thereby anchoring the prosthesis 1 to the vessel and preventing movement of the main vessel prosthesis 1 once it is deployed.

The main vessel prosthesis 1 may further include an attachment member 10 for securing the main prosthesis 1 to the wall of the main vessel to prevent migration of the main prosthesis 1 after it has been placed. The attachment member may comprise a bare-wire self-expanding zig zag stent and may include a plurality of radially disposed barbs for engaging the aorta 4.

In FIG. 1, the branched vessel system has a first aneurysm 8 positioned between the renal arteries 5 and the iliac arteries 6 and a second aneurysm 9 positioned in the ostium of the renal arteries 5. The main vessel prosthesis 1 provides a fluid seal against the main vessel 4 at positions proximal and distal of aneurysm 8, thereby excluding blood flow from the damaged area. Fenestrations 7 are provided so that blood flow is maintained to the renal arteries 5. Main vessel prosthesis 1 repairs aneurysm 8 but leaves aneurysm 9 exposed to blood flow and hemodynamic pressure.

Accordingly, a branch vessel prosthesis 11 may be provided in the renal artery 5 to exclude aneurysm 9. FIG. 1A shows a side view of the branched body lumen system of FIG. 1. The main vessel prosthesis 1 is disposed within the aorta and extends proximally and distally of the renal arteries 5. The prosthesis 1 has fenestrations 7 that are aligned with the renal arteries 5 to provide blood flow to the arteries. A branch vessel prosthesis 11 is disposed within the renal artery 5. A distal end of the branch vessel prosthesis 11 extends distally into the artery 5 and a proximal end 12 of the prosthesis 11 extends proximally through the fenestration 7 into the main vessel prosthesis 1.

FIG. 1B shows a cross-sectional view of the branched body lumen system of FIGS. 1 and 1A. The branch vessel prosthesis 11 comprises a generally fluid-impermeable graft material. The branch vessel prosthesis 11 may optionally comprise a stent 19 or a plurality of stents. The branch vessel prosthesis 11 seals against the renal artery at a position distal of aneurysm 9. The fenestration 7 forms a seal between the branch vessel prosthesis 11 and the main vessel prosthesis 1 and assists in anchoring the branch vessel prosthesis 11 in the vasculature. The main vessel prosthesis 1 and the branch vessel prosthesis 11 effectively exclude aneurysm 9.

Various graft materials and configurations may be used for either the main vessel prosthesis 1 or the branch vessel prosthesis 11. Graft configurations include, but are not limited to films, coatings, sheets of biocompatible fabrics, non-woven materials and porous materials.

Examples of biocompatible polymers from which porous sheets can be formed include polyesters, such as poly(ethylene terephthalate), polylactide, polyglycolide and copolymers thereof; fluorinated polymers, such as polytetrafluoroethylene (PTFE), expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments.

In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. Thus, any polymer that may be formed into a porous sheet can be used to make a graft material, provided the final porous material is biocompatible. Polymers that can be formed into a porous sheet include polyolefins, polyacrylonitrile, nylons, polyaramids and polysulfones, in addition to polyesters, fluorinated polymers, polysiloxanes and polyurethanes as listed above. Preferably the porous sheet is made of one or more polymers that do not require treatment or modification to be biocompatible.

The graft material may include a biocompatible polyurethane. Examples of biocompatible polyurethanes include THORALON® (Thoratec, Pleasanton, Calif.), BIOSPAN®, BIONATE®, ELASTHANE™, PURSIL™ and CARBOSIL™ (Polymer Technology Group, Berkeley, Calif.). As described in U.S. Patent Application Publication No. 2002/0065552, incorporated herein by reference, THORALON® is a polyetherurethane urea blended with a siloxane-containing surface modifying additive. Specifically, the polymer is a mixture of base polymer BPS-215 and an additive SMA-300.

The graft material may also include extracellular matrix materials. The "extracellular matrix" is typically a collagen-rich substance that is found in between cells in animal tissue and serves as a structural element in tissues. Such an extracellular matrix is preferably a complex mixture of polysaccharides and proteins secreted by cells. The extracellular matrix can be isolated and treated in a variety of ways. Following isolation and treatment, it is referred to as an "extracellular matrix material," or ECMM. ECMMs may be isolated from submucosa (including small intestine submucosa), stomach submucosa, urinary bladder submucosa, tissue mucosa, renal capsule, dura mater, liver basement membrane, pericardium or other tissues.

Purified tela submucosa, a preferred type of ECMM, has been previously described in U.S. Pat. Nos. 6,206,931, 6,358,284 and 6,666,892 as a bio-compatible, non-thrombogenic material that enhances the repair of damaged or diseased host tissues. U.S. Pat. Nos. 6,206,931, 6,358,284 and 6,666,892 are incorporated herein by reference. Purified submucosa extracted from the small intestine ("small intestine submucosa" or "SIS") is a more preferred type of ECMM for use in this invention. Another type of ECMM, isolated from liver basement membrane, is described in U.S. Pat. No. 6,379,710, which is incorporated herein by reference. ECMM may also be isolated from pericardium, as described in U.S. Pat. No. 4,502,159, which is also incorporated herein by reference.

In addition to xenogenic biomaterials, such as SIS, autologous tissue can be harvested as well. Additionally Elastin or Elastin Like Polypetides (ELPs) and the like offer potential as a material to fabricate the covering or frame to form a device with exceptional biocompatibility. Another alternative would be to use allographs such as harvested native valve tissue. Such tissue is commercially available in a cryopreserved state. In addition, a bare metal stent or a covered stent could be coated with an anti-restenotic agent, such as paclitaxel, sirilomis or other equivalent. In addition, the graft can be coated with an anti-thrombogenic agent, such as heparin.

The graft may be attached to a stent by various means. The graft material may be attached to the stent by stitching, for example by using a monofilament or braded suture material.

The graft material also may be affixed to the stent by dipping the stent in a liquefied polymer and allowing the polymer to solidify into a film. The liquefied polymer may be a molten polymer or a polymer or pre-polymer before curing or cross-linking occurs.

Figure 2B:
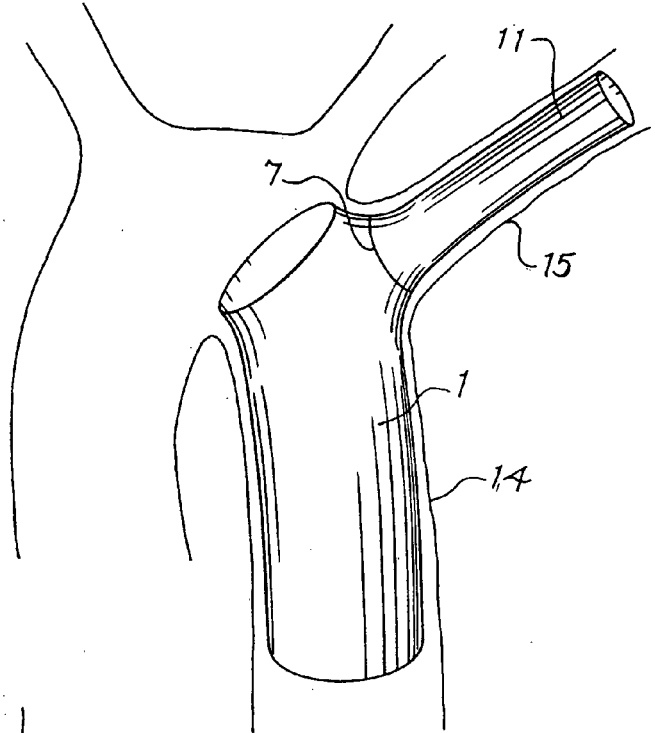
FIG. 2B is a partial cross-sectional view of a main vessel prosthesis in the descending aorta with a branch vessel prosthesis extending through a fenestration into the left subclavian artery.
Figure 2C:
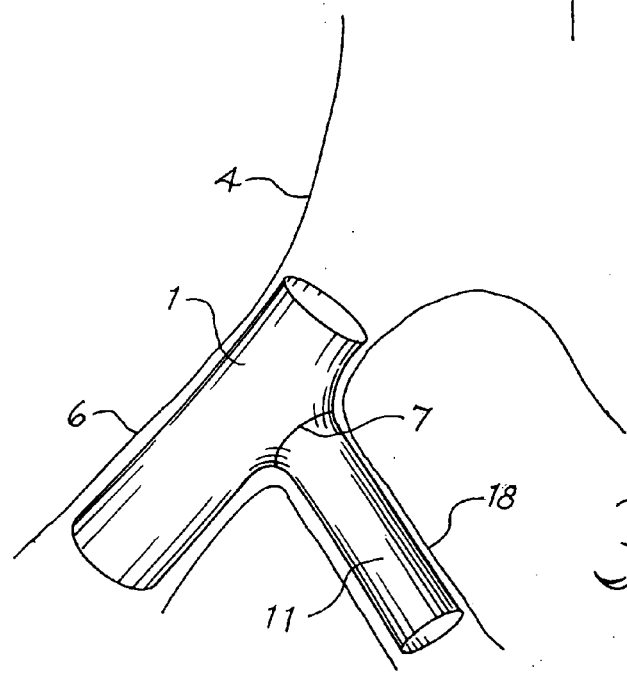
FIG. 2C is a partial cross-sectional view of a main vessel prosthesis in an iliac artery with a branch vessel prosthesis extending into the hypogastric artery.

FIGS. 2A-2C illustrate additional applications for prosthesis systems according to an aspect of the invention. In FIG. 2A, a main vessel prosthesis 1 is disposed partially within the aortic arch and within the thoracic aorta 14. The prosthesis 1 has fenestrations 7 that generally align with the left subclavian artery 15 and the left common carotid artery 16. FIG. 2B shows a main vessel prosthesis 1 having a fenestration 7 that aligns with the left subclavian artery 15. A branch vessel prosthesis 11 is provided and extends into the left subclavian artery 15. The branch vessel prosthesis 11 is secured to the main vessel prosthesis 11 through fenestration 7. FIG. 2C shows a main vessel prosthesis 1 disposed within an iliac artery 6. The prosthesis 1 has a fenestration 7 that aligns with the hypogastric artery 18. A branch vessel prosthesis 11 is provided and extends into the hypogastric artery 18. The branch vessel prosthesis 11 is secured to the main vessel prosthesis 1 through fenestration 7. Numerous other applications for the prosthesis systems described herein are contemplated and are included within the scope of the present invention.

In FIG. 3, a branch vessel prosthesis 11 is deployed within a branch vessel and through the fenestration 7 of a main vessel prosthesis 1. The fenestration 7 may comprise a reinforcing member 29. The reinforcing member 29 at least partially surrounds a perimeter of the fenestration 7 and is configured to engage the branch vessel prosthesis 11. The member 29 helps reinforce the connection and the seal between the main vessel prosthesis 1 and the branch vessel prosthesis 11. The reinforcing member 29 may comprise a metal ring or gasket, and may comprise, for example, stainless steel or nitinol.

The branch vessel prosthesis 11 has a proximal end 30 and a distal end 32. The prosthesis 11 comprises a generally tubular body portion 33 and a flareable proximal end portion 36. The body portion 33 and the flareable portion 36 are radially disposed about an axis A. The body portion 33 is configured to extend distally into the branch lumen. The flareable portion 36 is configured to extend proximally into the ostium of the branch vessel. In FIG. 3, the flareable portion 36 extends proximally through the fenestration 7 and flares radially outwardly into the lumen of the main vessel prosthesis 1. Preferably, at least a part of the flareable portion 36 has a diameter that is greater than the diameter of the fenestration 7. A bending portion 50 is disposed intermediate the flareable portion 36 and the body portion 33. The bending portion 50 is configured to bend to allow the flareable portion 36 to flare.

The prosthesis 11 further comprises a coupling portion 38. The coupling portion is disposed intermediate the flareable portion 36 and the body portion 33. The body portion 33 is generally longer than the coupling portion 38. For example, the body portion 33 may be five to seven times longer than the coupling portion 38. The coupling portion 38 is configured to engage the fenestration 7 of the main vessel prosthesis 1 when the branch vessel prosthesis 11 is deployed. When deployed, the coupling portion 38 is in mechanical communication with the main vessel prosthesis 1.

The branch vessel prosthesis 11 may comprise a suitable biocompatible graft material, as described above. Additionally, or alternatively, the prosthesis 11 may comprise one or more stents 19, as described above. The stents 19 may be fastened to the inner, the outer, or both surfaces of the graft. The graft material may cover the entire prosthesis or it may cover only a portion of the prosthesis. The stents 19 may be balloon-expandable or self-expanding. Imageable markers 43, such as radiopaque markers, may be attached to or integral with the prosthesis 11. For example, an imageable marker 43 may be provided and configured to indicate the bending portion 50 or the coupling portion 38.

Self-expanding stents can be made of stainless steel, materials with elastic memory properties, such as NITINOL, or any other suitable material. A suitable self-expanding stent includes Z-STENTS®, which are available from Cook, Incorporated, Bloomington, Ind. USA. Balloon-expandable stents may be made of stainless steel (typically 316LSS, CoCr, Etc.). A balloon-expandable stent or stent portion may be combined with a self-expanding stent or stent portion. For example, the prosthesis 11 may comprise a self-expanding body portion 33 and a balloon-expandable flareable portion 36. Alternatively, the prosthesis may comprise a self-expanding flareable portion 36 and a balloon-expandable body portion 33.

The body portion 33 preferably possesses a high degree of flexibility and resiliency. During delivery, the prosthesis 11 must be capable of tracking tortuous body lumina. Additionally, the prosthesis 11 must be sufficiently resilient to allow for ease of balloon expansion. In use, the body portion 33 of prosthesis 11 is exposed primarily to radial compression due to luminal contraction and expansion. The body portion 33 is not exposed to significant crushing or bending loads. Accordingly, the body portion 33 does not require a high degree of crush-resistance.

The flareable portion 36 preferably possesses a high degree of flexibility and resiliency as well. To deploy the branch vessel prosthesis 11, the flareable portion 36 is expanded and flared into the ostium of the branch vessel or into the lumen of the main vessel prosthesis 1. This is typically accomplished by using an expandable balloon to plastically deform or "iron" the flareable portion 36 from a tubular configuration into a flared configuration. If the flareable portion 36 is flexible, it will be relatively easy to flare. Conversely, if the flareable portion 36 is too rigid, it may be difficult to deploy. The flareable portion 36 does not require a high degree of crush-resistance because once the prosthesis 11 is deployed, the flareable portion 36 does not receive significant loading.

The coupling portion 38, on the other hand, preferably comprises a high degree of crush-resistance. In use, the cardiac cycle causes the main vessel prosthesis to pulse and to move along its axis. The distal end of the branch vessel prosthesis 11 is anchored within the branch lumen and the proximal end of the prosthesis 11 is anchored by the main vessel prosthesis 1 within the fenestration 7. As the main vessel prosthesis 1 pulses, it exerts a concentrated stress on the coupling portion 38 through the fenestration 7. This stress is particularly great where the fenestration 38 comprises a reinforcing member 29 such as a nitinol ring. The stress causes the prosthesis to bend, resulting in tensile, compression, and shear strain in the region adjacent the fenestration. Over time, this pulsatile stress can cause the coupling portion 38 to plastically deform and to crush under the weight of the main vessel prosthesis.

It is important to note that crush-resistance, as used herein, is not synonymous with radial strength. The radial strength of an expanded prosthesis is a measure of its ability to withstand elastic deformation when exposed to a uniform distributed radial stress. As noted above, the crush-resistance of an expanded prosthesis, on the other hand, is a measure of its ability to withstand plastic deformation when exposed to a concentrated and localized stress that includes bending. A prosthesis may comprise significant radial strength but have poor crush-resistance. Conversely, a prosthesis may comprise very low radial strength but have high crush-resistance.

Figure 4:
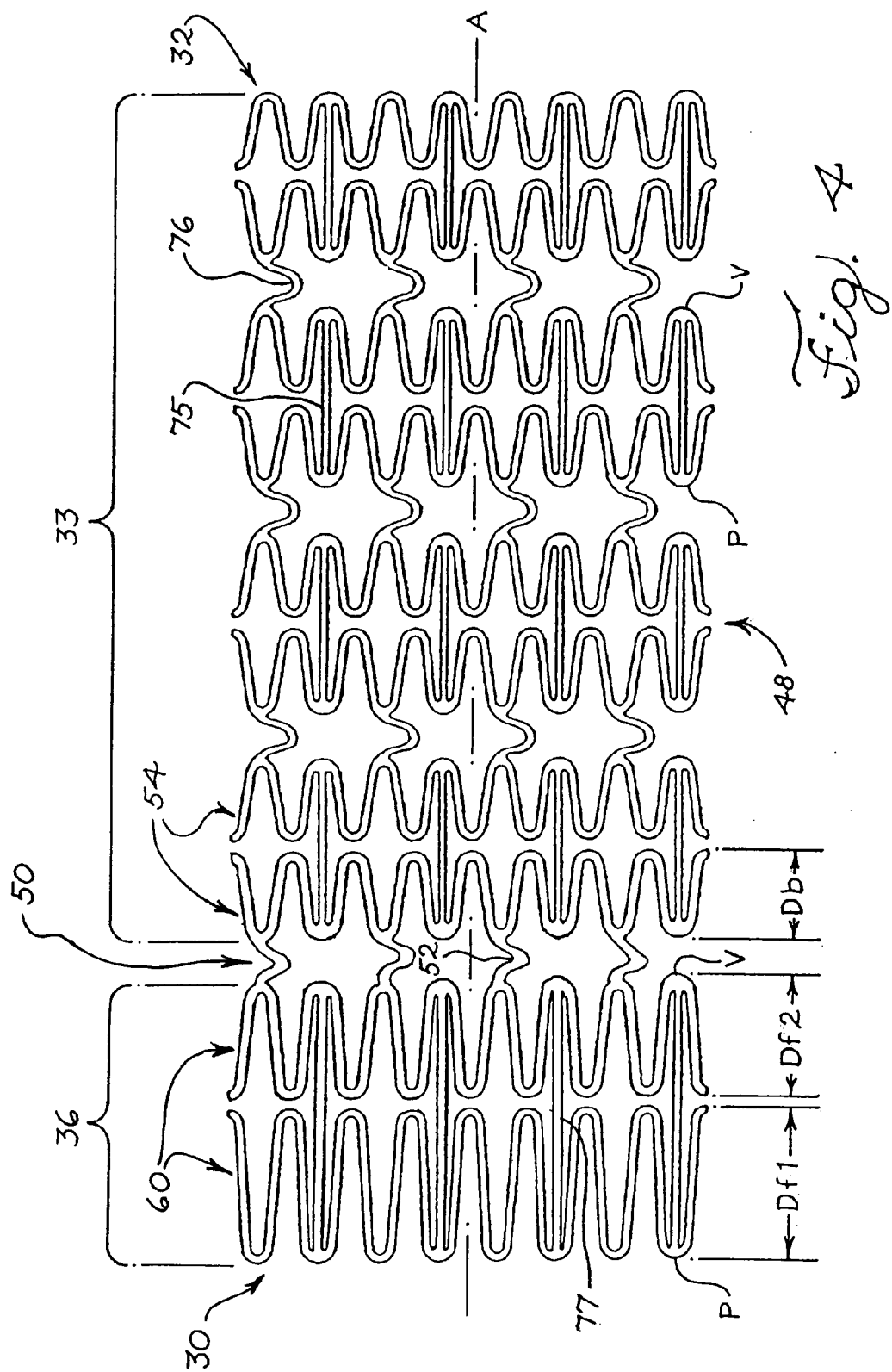
FIGS. 4 through 4D illustrate partial views of stent configurations that incorporate various aspects and features within the scope of the present invention.

A branch vessel prosthesis 11 may be provided that includes a stent 48. FIG. 4 shows a partial view of a stent 48 according to an aspect of the invention. The stent 48 is preferably balloon-expandable although a self-expanding or a hybrid balloon/self-expanding stent may be provided. The branch vessel prosthesis 11 may optionally include a graft that has been attached to the stent as described above. The prosthesis 11 is suitable for being deployed in the ostium of a vessel system. The prosthesis 11 may be used independently, for example to support or to stent the ostium of the branch vessel. Alternatively, the prosthesis 11 may be used in conjunction with a main vessel prosthesis, as described above.

The stent 48 is generally tubular and has a proximal end 30 and a distal end 32. The stent 48 includes a flareable portion 36 and a body portion 33. The flareable portion 36 is disposed at the proximal end 30 of the stent 48. The body portion 33 is disposed distally of the flareable portion 36. The body portion 33 and the flareable portion 36 are radially disposed about an axis A. The body portion 33 is coupled to the flareable portion 36 via bending portion 50. The bending portion 50 is configured to bend to allow the flareable portion 36 to flare radially outwardly during deployment.

The body portion 33 comprises a stent configuration that includes at least two longitudinally interconnected body stent cells 54. In the embodiment shown in FIG. 4, the body portion 33 includes at least eight interconnected cells 54. The body portion 33 may include a fewer or a greater number of cells 54 according to the particular application. Each of the cells 54 may include a substantially circular stent ring comprising an endless undulating pattern, as shown in FIG. 4. Each of cells 54 is radially disposed about the axis A and longitudinally disposed with respect to another cell 54. Each of the cells 54 includes a plurality of proximally-oriented peaks P and a plurality of distally-oriented valleys V. The body cells 54 are arranged in an alternating pattern so that peaks in one body cell 54 are axially-aligned with valleys in an adjacent body cell 54. Each of the body cells 54 comprises an axial dimension Db. In the embodiment shown in FIG. 4, each of the body cells 54 has a substantially equal axial dimension Db.

Adjacent body cells 54 are interconnected by struts 75 and/or connection members 76. In FIG. 4, axially-oriented struts 75 interconnect adjacent body cells 54 between a peak of one body cell 54 and a valley of a distally-adjacent body cell 54. Connection members 76 interconnect adjacent body cells 54 between a valley of one body cell 54 and a peak of a distally-adjacent body cell 54. Struts 75 and connection members 76 provide structural support and elasticity to the body portion 33.

Flexibility of the body portion 33 along the body cells 54 may be provided in many ways. For example, the shape of connection members 76 may be varied to affect the flexibility of the body portion 33. The connection member 76 may comprise an "I" shape, a "V" shape, an "S" shape, a "W" shape, or any other arcuate or undulating shape. The number and configuration of the struts 75 can also be varied to affect the flexibility of the body portion 33. For example, increasing the frequency of struts 75 results in generally lower flexibility while decreasing the frequency of struts 75 results in generally higher flexibility. Further, the body portion 33 may be made more flexible by decreasing the thickness of any of the struts 75, or connection members 76.

The flareable portion 36 comprises a stent configuration that includes at least two longitudinally interconnected flare cells 60. Each of the flare cells 60 may include a substantially circular stent ring comprising an endless undulating pattern, as shown in FIG. 4. Each of the flare cells 60 is radially disposed about the axis A and longitudinally disposed with respect to another cell 60. Each of the cells 60 includes a plurality of proximally-oriented peaks P and a plurality of distally-oriented valleys V. The flare cells 60 are arranged in an alternating pattern so that peaks in a flare cell 60 are axially-aligned with valleys in an adjacent flare cell 60. The flare cells 60 may be arranged so that the peaks in the distal-most flare cell 60 are aligned with the valleys in the proximal-most body cell 54. Each of the flare cells 60 comprises an axial dimension Df1, Df2.

According to an aspect of the present invention, the axial dimension Df1, Df2 of the flare cells 60 is generally greater than the axial dimension Db of the body cells 54. Because the axial dimension Df1, Df2 of the flare cells 60 is generally greater than the axial dimension Db of the body cells 54, the flare cells 60 will tend to be more resilient and will be expandable to a larger diameter than the body cells 54. The proximal peaks of the flareable portion 36 are unattached and are free to expand and separate, thereby permitting the flareable portion 36 to flare-out in the expanded configuration.

As shown in FIG. 4, the axial dimension Df1 of the proximal-most flare cell 60 is generally greater than the axial dimension Df2 of the distal-most flare cell 60. Accordingly, the proximal-most flare cell 60 will be more resilient and will be expandable to a larger diameter than the distal-most flare cell 60. The flare cells 60 are arranged so that the axial dimension of the cells increases proximally with the stent configuration. The axial dimensions of each of the flare cells can be selected to provide a desired flare profile upon deployment.

According to an aspect of the invention, the axial dimension Df1, Df2 of each of the flare cells 60 is at least 10% greater or at least 20% greater than the axial dimension Db of the body cells 54. In a preferred embodiment, the axial dimension Df1, Df2 of each of the flare cells 60 is at least 40% greater than the axial dimension Db. The axial dimension Df1 of the proximal-most flare cell 60 may be at least 10% or at least 20% greater than the axial dimension Df2 of the distal-most flare cell 60. In a preferred embodiment, the axial dimension Df1 is at least 25% greater than axial dimension Df2.

Adjacent flare cells 60 are interconnected by struts 77. In the embodiment shown in FIG. 4, axially-oriented struts 77 interconnect adjacent flare cells 60 between a peak of the proximal-most flare cell 60 and a valley of the distal-most flare cell 60. Struts 77 provide structural support and stiffness to the flareable portion 36.

The flareable portion 36 is coupled to the body portion 33 through the bending portion 50. The bending portion 50 minimizes the stress imposed by the flareable portion 36 on the tubular portion 33 in the expanded configuration by providing a region of relative flexibility. Increasing the flexibility of bending portion 50, increases the ability of the flareable portion 36 to flare-out in the expanded configuration. Flaring of the flareable portion 36 is thus facilitated by the bending portion 50.

The bending portion 50 may comprise at least two bendable connector elements 52 that connect the flareable portion 36 to the body portion 33. The number of connector elements 52, and therefore the frequency of the points of attachment between the flareable portion 36 and the body portion 33 can be varied to facilitate bending in the bending portion 50.

Figure 4B:
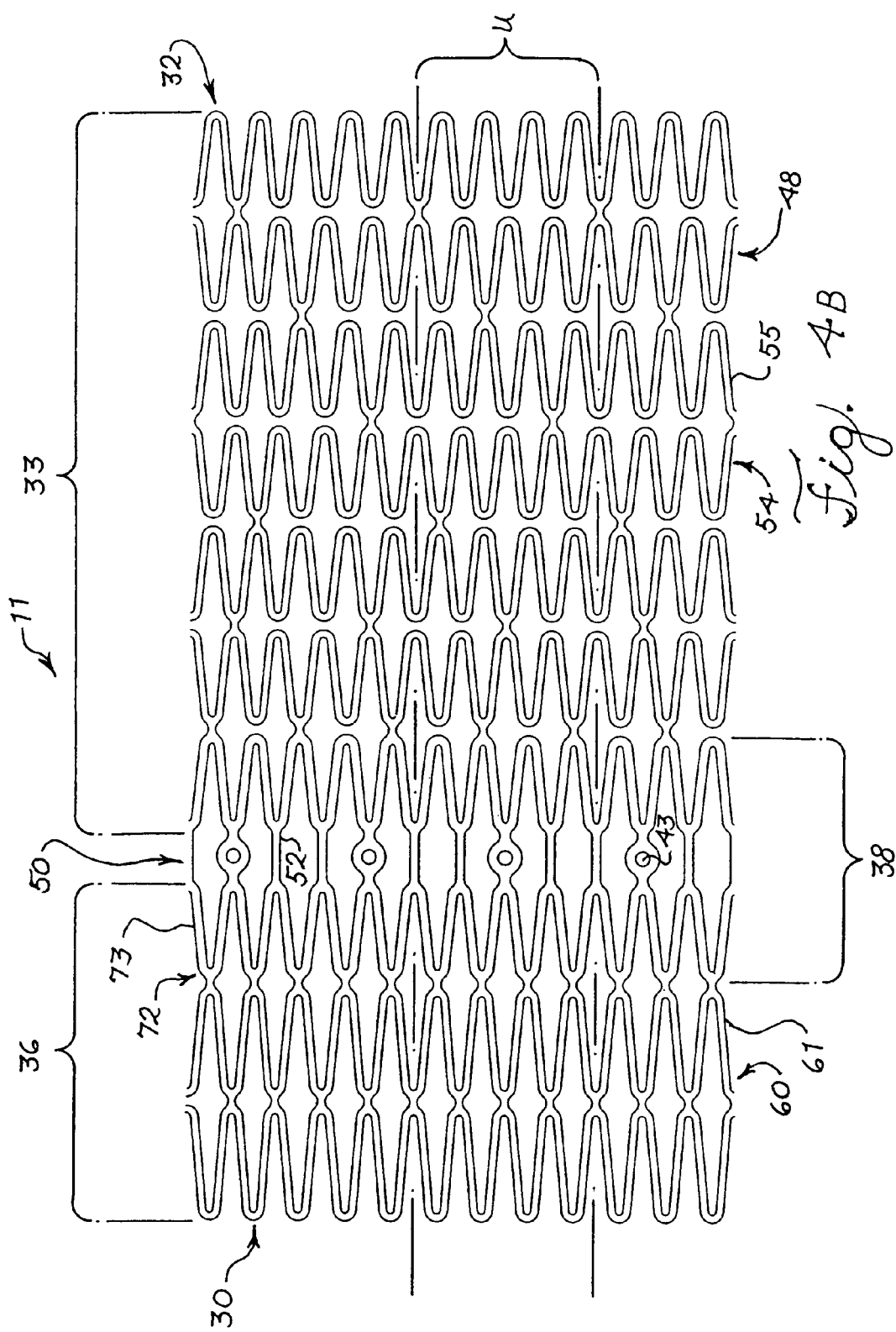

Connector elements 52 may be non-linear or arcuate in shape, as illustrated in FIG. 4, or may be generally linear as illustrated in FIGS. 4A-C. Connector elements 52 may, for example, comprise a "V" shape, an "S" shape, or a "W"

shape. Where the prosthesis 11 comprises a graft material, for example a coating or film of plastic (such as Thoralon), the bending portion 50 may include the graft. For example, the flareable portion 36 and the body portion 33 may comprise separate stent structures that are longitudinally displaced from each other and are connected through the graft. In FIG. 4, the connector elements 52 are disposed between a valley of the distal-most flare cell 60 and a peak of the proximal-most body cell 54.

According to an aspect of the invention, the flare struts 77 may be thicker than the body struts 75. The flare struts 77 may be circumferentially thicker than the body struts 75 and have a thickness measured along the circumference of the stent 48 that is greater than a like thickness of the body struts 75. In other words, the flare struts 77 may be wider than the body struts 75. The flare struts 77 may alternatively or additionally be radially thicker than the body struts 75. That is to say, the flare struts 77 may have a thickness measured along a radius of the stent 48 that is greater than a like thickness of the body struts 75. The flare struts 77 may be at least 10% or at least 20% thicker than the body struts 75. In a preferred embodiment, the flare struts 77 are at least 25% thicker than the body struts.

Thickening the flare struts 77 in relation to the body struts 75 will generally reduce the flexation and increase the stiffness of the flareable portion 36 in relation to the body portion 33. Because the proximal peaks of the flareable portion 36 are unattached and are free to expand and separate, the flareable portion 36 is most flexible and resilient at its proximal end. Further, because the axial dimension Df1 of the proximal-most flare cell 60 is greater than the axial dimension Df2 of the distal-most flare cell 60, the flexibility of the proximal-most cell will be generally greater and the stiffness will be generally less than that of the distal-most flare cell. Consequently, in the embodiment shown in FIG. 4, the stiffness of the flareable portion 36 increases distally towards the bending portion 50, thereby forming a generally crush-resistant zone at the distal end of the flareable portion 36. This crush-resistant zone is desirable, particularly where the prosthesis 11 requires additional strength and support, for example in the ostium of the branch vessel, or at the region in contact with the fenestration 7 of a main vessel prosthesis 1.

FIG. 4A illustrates another stent 48 according to an aspect of the present invention. The stent 48 includes a flareable portion 36 and a body portion 33. The flareable portion 36 is disposed at the proximal end 30 of the stent 48. The body portion 33 is disposed distally of the flareable portion 36. The body portion 33 and the flareable portion 36 are radially disposed about an axis A. The body portion 33 is coupled to the flareable portion 36 through bending portion 50. The bending portion 50 is configured to bend to allow the flareable portion 36 to flare radially outwardly.

The stent 48 further comprises a coupling portion 38. The coupling portion 38 is positioned generally intermediate the body portion 33 and the flareable portion 36 and may comprise the bending portion 50. The coupling portion 38 is configured to support the ostium of a branch vessel or to engage the fenestration 7 in the main vessel prosthesis 1. The main vessel prosthesis 1 can be secured to the branch vessel prosthesis 11 via the coupling portion 38.

The stent 48 comprises at least one imageable marker 43. The imageable marker 43 is disposed on the branch vessel prosthesis 11 and is configured to indicate a portion of the prosthesis 11. The imageable marker 43 comprises a substance that is imageable in the body using, for example fluoroscopic techniques. For example, the marker may comprise gold. In FIG. 4A, the stent 48 comprises a plurality of markers 43 disposed radially about the prosthesis that generally indicate the coupling portion 38. Each of the imageable markers 43 is in the shape of an eyelet.

The body portion 33 comprises a plurality of axially-oriented interconnected body cells 54. Each body cell 54 may include a substantially circular stent ring comprising an endless undulating pattern. Each body cell 54 comprises a plurality of interconnected body struts 55. Adjacent body struts 55 interconnect to form proximally-oriented peaks P and distally-oriented valleys V. Body cells 54 have an axial dimension Db. Adjacent body cells 54 are interconnected by a plurality of axially-oriented struts 75 and/or connection members 76, as previously described.

The flareable portion 36 comprises at least two flare cells 60. The flare cells 60 are configured to flare when the prosthesis 11 is in an expanded configuration. Each flare cell 60 includes a substantially circular stent ring comprising an endless undulating pattern. Each flare cell 60 comprises a plurality of interconnected flare struts 61. Adjacent flare struts 61 form proximally-oriented peaks and distally-oriented valleys. The axial dimension Df1, Df2 of the flare cells 60 is generally greater than the axial dimension Db of the body cells 54, as described above. Further, the axial dimension Df1 of the proximal-most flare cell 60 is generally greater than the axial dimension Df2 of the distal-most flare cell.

The bending portion 50 comprises a plurality of bendable connector elements 52. Connector elements 52 connect the flareable portion 36 to the body portion 33. The number of connector elements 52, and therefore the frequency of the points of attachment between the flareable portion 36 and the body portion 33 can be varied to facilitate bending in the bending portion 50. The shape of the connector elements 52 can also be modified, as described above to selectively increase or decrease flexibility in the bending portion.

The coupling portion 38 is disposed intermediate the body portion 33 and the flareable portion 36. The coupling portion 38 comprises coupling cells 72. Each coupling cell 72 may include a substantially circular stent ring comprising an endless undulating pattern. Each coupling cell 72 comprises a plurality of interconnected struts 73. Adjacent coupling struts 73 form proximally-oriented peaks and distally-oriented valleys. In FIG. 4A, the stent 48 includes two coupling cells 72: one disposed proximally of the bending portion 50, and the other disposed distally of the bending portion 50.

Figure 5:
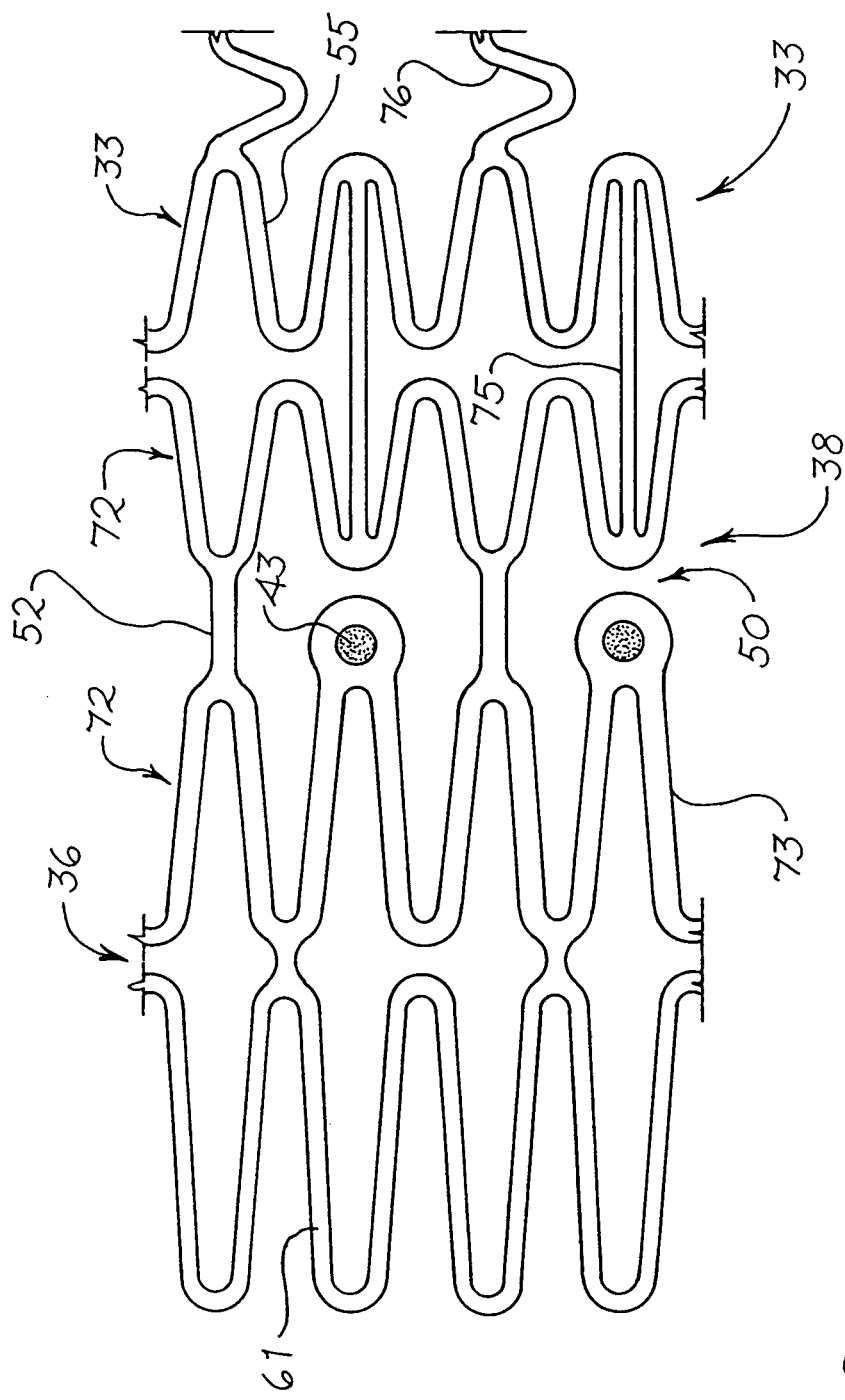
FIG. 5 is a partial view of a proximal portion of a stent configuration having a crush-resistant zone.

The coupling portion 38 is more crush-resistant than the body portion 33 and the flareable portion 36. For example, the coupling struts 73 may be generally thicker than body struts 55 and flare struts 61, as shown in FIGS. 4A and 5. Additionally, connector elements 52 may be thicker than body struts 55 and flare struts 61 as shown in FIG. 4A and FIG. 5. Increasing the thickness of coupling struts 73 and the connector elements 52 increases the stiffness of the coupling portion 38. Consequently, the coupling portion 38 will be more resistant to bending and plastic deformation. The body portion 33 and the flareable portion 36, on the other hand comprise struts 55, 61 that are thinner and are consequently more flexible.

The coupling portion 38 preferably comprises struts 73 and connector elements 52 that are at least 10% thicker than the body struts 55 or the flare struts 61, or the coupling portion 38 may comprise struts 73 and connector elements 52 that are at least 20% thicker than the body struts 55 and the flare struts 61. According to a preferred embodiment, the coupling portion 38 comprises struts 73 and connector elements 52 that are at least 25% thicker than the body struts 55 and the flare struts 61. The body struts 55 may have a thickness that is generally equal to a thickness of the flare struts 61. Alternatively, the body struts 55 may have a thickness that is less than or greater than a thickness of the flare struts 61.

FIG. 5 shows a portion of the stent 48 of FIG. 4A, wherein the coupling struts 73 are circumferentially thicker than the body struts 55. The coupling struts 73 may alternatively or additionally be radially thicker than the body struts 55. As illustrated in FIGS. 4A and 5, the thickness of each strut 73 and/or connector element 52 may be generally longitudinally uniform. Alternatively, the struts 73 and/or connector elements 52 may have a longitudinally variable thickness. For example, the struts 73 and/or connector elements 52 could be configured so that a medial portion comprises a first thickness that is generally greater than a second thickness at each end.

FIGS. 4B-4D illustrate alternative stents 48 according to various aspects of the present invention. Each of the stents 48 includes a body portion 33, a proximally disposed flareable portion 36, a bending portion 50, and a coupling portion 38, as described above with respect to FIGS. 4, 4A and 5. The embodiments shown in FIGS. 4B and 4C include a plurality of radially disposed imageable markers 43 that are configured to indicate the coupling portion 38 of the prosthesis 11. The imageable markers 43 are in the shape of an eylet. The flareable portion 36 and the body portion 33 are connected at various points via the eylets 43 and via bendable connector elements 52.

In each of FIGS. 4B-4D, the stent 48 has a coupling portion 38 that is more crush-resistant than a body portion 33. For example, the coupling struts 73 may be circumferentially and/or radially thicker than the body struts 55. The stents 48 in FIGS. 4B-4D incorporate various additional features that can be used in the present invention. For example, the interconnection frequency between adjacent coupling cells 72 may be generally greater than the interconnection frequency between adjacent body cells 54. As used herein, "interconnection frequency" refers to the number of points of attachment between adjacent cells per unit.

In FIGS. 4B-4D, the interconnection frequency between the body cells 54 increases proximally along the stent 48. For example, as shown in FIG. 4B, the interconnection frequency increases from one connection per unit U at the distal end of the body 33 portion to two connections per unit U adjacent the coupling portion 38. The interconnection frequency between the coupling cells 72, on the other hand is four connections per unit. Because the interconnection frequency between the body cells 54 is relatively low, the body portion 33 will tend to be more flexible than the coupling portion. On the other hand, because the interconnection frequency between the coupling cells 72 is relatively high, the coupling portion 38 will be better equipped to receive and disperse contact loading from the fenestration 7, and will be generally more crush-resistant.

FIGS. 6 and 7 illustrate a device 80 for delivering and deploying a partially or entirely balloon expandable branch vessel prosthesis 11 into a body lumen. As shown in FIG. 6, the delivery device 80 used to place and deploy the branch vessel prosthesis 11 comprises a balloon catheter 82 having a proximal portion 84 and a distal portion 86. The distal portion 86 is configured to be percutaneously inserted into a patient to deliver the prosthesis 11 to a damaged or diseased body lumen. The proximal portion 84 remains outside of the patient and is manipulated by the operator during a procedure.

FIG. 7 shows a partial cross-sectional view of a distal portion 86 of the balloon catheter 82. The balloon catheter 82 comprises a guide wire lumen 96 and a balloon inflation lumen 97. The guidewire lumen 96 is adapted to receive a guidewire 98 during a procedure. The balloon inflation lumen 97 is adapted to deliver pressurized fluid to expand the balloon. As shown in FIG. 6, the proximal portion 84 of the delivery device 80 comprises a guidewire port 83 for inserting the guidewire 98 into the guidewire lumen 96 and a balloon inflation port 85 for introducing pressurized fluid into the inflation lumen 97.

The balloon catheter 82 further includes a stent loading area 88 and may include a stent positional indicator system 91 located on a distal portion 86 of the catheter 82. The stent-loading area 88 comprises an inflatable balloon 90. The prosthesis 11 is loaded onto the deflated balloon 90 in a compressed configuration. The positional indicator system 91 includes one or more positional indicators that correspond with various parts of the branch vessel prosthesis 11. For example, the positional indicator system 91 may include an indicator 92 on the catheter that corresponds with the coupling portion 38. The system 91 may further include indicators 93, 94 that correspond with the distal and proximal ends 30, 32 of the prosthesis 11 respectively. Indicators 92, 93, 94 may include radiopaque marker bands.

The positional indicator system 91 can be used in conjunction with other positional systems for deploying the branch vessel prosthesis 11. For example, the main vessel prosthesis 1 may include a positional indicator that indicates the position of the fenestration 7. During delivery and deployment, the indicator 92 may be coordinated with the fenestration indicator to ensure proper alignment and positioning of the branch vessel prosthesis 11 with respect to the main vessel prosthesis 1. Preferably, the positional indicators 92, 93, 94 are shaped so as to indicate the position and orientation of the branch vessel prosthesis 11 during and after deployment. The positional markers may be of any configuration to facilitate their visualization. For example, the positional markers may be v-shaped with one leg longer than the other.

In operation, the branch vessel prosthesis 11 is positioned about the unexpanded balloon on the catheter and crimped thereto so that desired portions of the branch vessel prosthesis 11 align with corresponding components of the positional indicator system 91. If the positional indicators 92, 93, 94 are disposed on the distal portion 86 of the catheter 82 within the balloon, the balloon 90 may comprise a generally transparent material so that the marker system 91 can be easily viewed during loading.

The balloon catheter 82 may comprise any balloon configuration suitable for expanding the prosthesis 11 and for flaring the flareable portion 36. For example, the balloon may comprise a first balloon portion for expanding the body portion 33 and the coupling portion 38, and a second balloon portion for further expanding the flareable portion 36. U.S. Published Patent Application Nos. 2005/02222668, 2005/0171598, and 2005/0149166, which have previously been incorporated by reference, disclose delivery systems for endoluminal prostheses having single and multiple balloons. The delivery systems disclosed therein could be used with the present invention.

FIGS. 8-10 illustrate various stages of deployment of the branch vessel prosthesis 11. A main vessel prosthesis 1 has previously been deployed within the main body lumen and is positioned so that fenestration 7 generally aligns with the opening of branch vessel 5. The main vessel prosthesis 1 can be deployed in any manner known in the art, including the method described in PCT Application WO 98/53761.

Once the main vessel prosthesis 1 has been deployed, the branch prosthesis delivery device 80 can be inserted via a surgical cut-down into an artery, or by percutaneous access techniques that are well known in the art. The branch vessel delivery device 80 is advanced into the desired position over a stiff wire guide using endoluminal interventional techniques. A guide wire 98 is introduced into an artery of the patient and advanced through the lumen of the main vessel prosthesis 1 until its tip is beyond the desired deployment region. For example, the guide wire 98 may be advanced into the lumen of the main vessel prosthesis 1 and distally through the fenestration 7 into the branch vessel 21. The delivery device 80 is then advanced over the guide wire 98 and into the body lumen until the prosthesis 11 is properly positioned in the branch vessel 5.

FIG. 8 shows the delivery device 80 positioned within the lumen of the main vessel prosthesis 1 with the branch vessel prosthesis 11 extending through the fenestration 7 into the branch vessel 5. Using standard radiographic techniques, the operator may ensure proper positioning by aligning the prosthesis 11 with the fenestration 7. For example, the main vessel prosthesis may comprise a positional indicator (not shown) that generally indicates the fenestration 7. Radiopaque marker 43, located on the stent, and/or positional indicator 92 located on the delivery device 80, may be coordinated with a fenestration indicator to ensure proper positioning and orientation of the branch vessel prosthesis 11 with respect to the main vessel prosthesis 1. Once the prosthesis 11 is properly positioned, the delivery device 80 is ready for deployment.

FIG. 9 shows the delivery device 80 with the prosthesis 11 in a partially-deployed state. In FIG. 9, the balloon catheter 82 comprises a single balloon 90, however multiple-balloon configurations may be used. Pressurized fluid is charged to the balloon 90 via the balloon inflation lumen (not shown), causing the balloon 90 to inflate to a first expanded state. The balloon 90 expands, causing the prosthesis 11 to radially expand so that the distal end 32 of the prosthesis 11 engages the inner lumen of the branch vessel 5. The distal end 32 of the prosthesis 11 may comprise barbs (not shown) for securing the prosthesis to the branch vessel 5. At this point, the prosthesis 11 has a generally tubular shape. The flareable portion 36 is not yet flared and the coupling portion 38 is not yet coupled to the main vessel prosthesis 1.

In FIG. 10, the operator has inflated the balloon 90 to expand it to a second expanded state, thus causing the bending portion 50 of the prosthesis 11 to bend and the flareable portion 36 to flare. As the balloon 90 expands, the coupling portion 38 engages the fenestration 7. Where the prosthesis 11 comprises a graft, the fenestration 7 may form a fluid seal between the main vessel prosthesis 1 and the branch vessel prosthesis 11. At this point, the delivery device 80 is ready to be removed. The balloon 90 is deflated and the catheter 82 is withdrawn from over the guidewire 98. A separate balloon catheter may optionally be used at this point to further mold and iron the flareable portion 36 to ensure proper engagement between the main vessel prosthesis 1 and the branch vessel prosthesis 11. The deployment method, including the initial expanding step and the flaring step may be performed using a single delivery catheter as described above. Alternatively, the method could be performed using multiple delivery and balloon catheters.

Throughout this specification various indications have been given as to preferred and alternative embodiments of the invention. However, it should be understood that the invention is not limited to any one of these. It is therefore intended that the foregoing detailed description be regarded as illustrative rather than limiting, and that it be understood that it is the appended claims, including all equivalents, that are intended to define the spirit and scope of this invention.

What is claimed is:

1. An endoluminal prosthesis system for a branched body lumen, the system comprising:
   a branch vessel prosthesis deployable within a branch vessel body lumen and comprising a stent having a generally tubular body portion, a flareable proximal end portion, and a coupling portion disposed intermediate the body portion and the flareable portion, wherein the coupling portion is more crush-resistant than the body portion.

2. The system of claim 1, wherein:
   the body portion has a stent configuration comprising at least one body stent ring including a plurality of interconnected body struts; and
   the flareable end portion has a stent configuration comprising at least one flare stent ring including a plurality of interconnected flare struts.

3. The system according to claim 2, wherein the coupling portion has a stent configuration comprising at least one coupling stent ring disposed between a flare stent ring and a body stent ring, the at least one coupling stent ring including a plurality of interconnected coupling struts.

4. The system according to claim 3, wherein the coupling portion comprises a plurality of coupling stent rings.

5. The system according to claim 3, wherein the coupling struts are thicker than the body struts.

6. The system according to claim 5, wherein the coupling struts are at least one of:
   circumferentially thicker than the body struts; and
   radially thicker than the body struts.

7. The system according to claim 5, wherein the coupling struts are one of at least 10% thicker, at least 20% thicker, and at least 25% thicker than the body struts.

8. The system according to claim 3, wherein the coupling struts are thicker than the flare struts.

9. The system according to claim 2, wherein:
   the body portion comprises a plurality of longitudinally-interconnected body stent rings;
   the coupling portion comprises a plurality of longitudinally-interconnected coupling stent rings; and
   the interconnection frequency between the coupling stent rings is greater than the interconnection frequency between the body stent rings adjacent the coupling portion.

10. The system according to claim 2, wherein:
   the body portion comprises a plurality of body stent rings, each having an axial dimension;
   the flareable end portion comprises a plurality of flare stent rings, each having an axial dimension; and
   the axial dimension of each of the flare stent rings is greater than the axial dimension of each of at least two body stent rings adjacent the flareable end portion.

11. The system according to claim 10, wherein the axial dimension of each of the flare stent rings is one of at least 10% greater, at least 20% greater, and at least 40% greater than the axial dimension of each of at least two body stent rings adjacent the flareable end portion.

12. The system according to claim 10, wherein the axial dimension of the flare stent rings increases proximally with the flareable stent configuration.

13. The system according to claim 12, wherein the axial dimension of the proximal-most flare stent ring is one of at least 10%, at least 20%, and at least 25% greater than the axial dimension of the distal-most flare stent ring.

14. The system according to claim 2, wherein:
   the body portion comprises a plurality of body stent rings that are interconnected by a plurality of body connector struts;

the flareable end portion comprises a plurality of flare stent rings that are interconnected by a plurality of flare connector struts; and the flare connector struts are thicker than the body connector struts.

15. The system according to claim 14, wherein each of the flare connector struts are at least one of:

circumferentially thicker than the body connector struts; and radially thicker than the body connector struts.

16. The system according to claim 14, wherein the flare connector struts are one of at least 10% thicker, at least 20% thicker, and at least 25% thicker than the body connector struts.

17. The system according to claim 1, further comprising:

a main vessel prosthesis deployable within a main vessel body lumen and having a main prosthesis lumen and a fenestration for providing fluid communication between the main prosthesis lumen and the branch vessel body lumen;

wherein the coupling portion of the branch vessel prosthesis is sized and configured to engage the fenestration.

18. The system according to claim 17, further comprising a reinforcing member at least partially surrounding the perimeter of the fenestration and configured to engage the coupling portion of the stent.

19. The system according to claim 1, wherein the branch vessel prosthesis further comprises a graft.

20. The system according to claim 1, further comprising:

a main vessel prosthesis deployable within a main vessel body lumen and having a main prosthesis lumen and a fenestration for providing fluid communication between the main prosthesis lumen and the branch vessel body lumen; and a reinforcing member at least partially surrounding the perimeter of the fenestration and configured to engage the coupling portion of the stent;

wherein:

the body portion has a stent configuration comprising a plurality of longitudinally-interconnected body stent rings, each of the body stent rings including a plurality of interconnected body struts and having an axial dimension;

the flareable end portion has a stent configuration comprising a plurality of longitudinally-interconnected flare stent rings, each of the flare stent rings including a plurality of interconnected flare struts and having an axial dimension;

the coupling portion has a stent configuration comprising a plurality of longitudinally-interconnected coupling stent rings disposed between a flare stent ring and a body stent ring, each of the coupling stent rings including a plurality of interconnected coupling struts;

the interconnection frequency between the coupling stent rings is greater than the interconnection frequency between the body stent rings adjacent the coupling portion;

the coupling struts are thicker than the body struts;

the coupling struts are thicker than the flare struts;

the axial dimension of each of the flare stent rings is greater than the axial dimension of each of at least two body stent rings adjacent the flareable end portion;

the axial dimension of the flare stent rings increases proximally with the flareable stent configuration;

the body stent rings are interconnected by a plurality of body connector struts;

the flare stent rings are interconnected by a plurality of flare connector struts; and the flare connector struts are thicker than the body connector struts.

\* \* \* \* \*